United States Patent [19]

Masciadri

[11] Patent Number: 5,773,446
[45] Date of Patent: Jun. 30, 1998

[54] DIAMINO PYRIMIDINES

[75] Inventor: Raffaello Masciadri, Basel, Switzerland

[73] Assignee: Hoffmann-La Roche Inc., Nutley, N.J.

[21] Appl. No.: 758,993

[22] Filed: Dec. 2, 1996

[30] Foreign Application Priority Data

Dec. 4, 1995 [CH] Switzerland ............... 3425/95

[51] Int. Cl.$^6$ ............ C07D 405/06; A61K 31/505
[52] U.S. Cl. ............................. 514/275; 544/324
[58] Field of Search .................. 514/256, 275; 544/324

[56] References Cited

FOREIGN PATENT DOCUMENTS 051 879   11/1981   European Pat. Off. .

OTHER PUBLICATIONS

Anderson, W.K., and E.J. LaVoie, *J. Org. Chem.*, 38, 3832 (1973).
Anderson, W.K., and E.J. LaVoie, *Chem. Reviews*, 84, 221–223 (1984).
Manchand, P.S., et al., *J. Org. Chem.*, 57, 3531–3535 (1992).
Then et al. Chemical Abstracts vol. 121 Entry 2 71 337 (1994).

*Primary Examiner*—John M. Ford
*Attorney, Agent, or Firm*—George W. Johnston; Dennis P. Tramaloni; Alan P. Kass

[57] ABSTRACT

Compounds of formula I

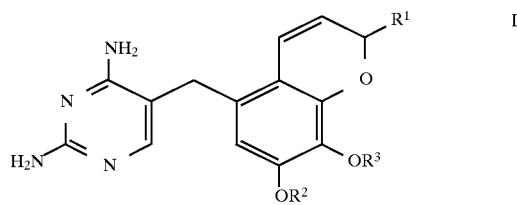

wherein either $R^1$ signifies straight-chain $C_{5-10}$-alkyl, branched $C_{3-5}$-alkyl, $C_{3-6}$-cycloalkyl or $C_{3-5}\omega$-carboxyalkyl and $R^2$ and $R^3$ signify $C_{1-5}$-alkyl; or $R^1$ signifies hydrogen, $R^2$ signifies $C_{3-5}\omega$-carboxyalkyl and $R^3$ signifies $C_{1-5}$-alkyl;

or their pharmaceutically acceptable acid addition salts have antibiotic properties and can be used in the control or prevention of infectious diseases.

13 Claims, No Drawings

DIAMINO PYRIMIDINES

The present invention is concerned with compounds of formula I

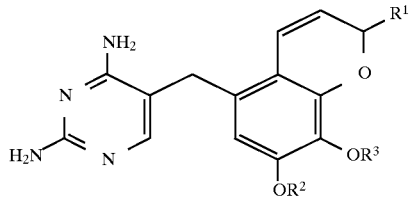

wherein either

R$^1$ is straight-chain C$_{5-10}$-alkyl, branched C$_{3-5}$-alkyl, C$_{3-6}$-cycloalkyl or C$_{3-5}$-ω-carboxyalkyl and each of R$^2$ and R$^3$ is C$_{1-5}$-alkyl; or R$^1$ is hydrogen, R$^2$ is C$_{3-5}$ω-carboxyalkyl and R$^3$ is C$_{1-5}$-alkyl;

or their pharmaceutically acceptable acid addition salts.

These compounds are novel and have valuable antibiotic properties. They can be used in the control or prevention of infectious diseases in mammals, both humans and non-humans. In particular, they exhibit a pronounced antibacterial activity, even against multiresistant, gram-positive strains and against opportunistic pathogens such as e.g. *Pneumocystis carinii*. The compounds can also be administered in combination with known antibacterially active substances, exhibiting synergistic effects.

Typical combination partners are e.g. sulfonamides or other inhibitors of enzymes which are involved in folic acid biosynthesis such as, for example, pteridine derivatives can be admixed in different proportions with the compounds of formula I or their salts.

Objects of the present invention are compounds of formula I, their readily hydrolyzable esters and pharmaceutically acceptable salts per se and for use as therapeutically active substances; medicaments based on these substances, optionally in combination with sulfonamides, and their production; the use of these substances as medicaments and for the production of antibacterially active medicaments; as well as the manufacture of the compounds of formula I and their pharmaceutically acceptable salts and intermediates for their manufacture.

The terms C$_{1-5}$, C$_{3-5}$ and C$_{5-10}$ denote the number of carbon atoms in the groups in question. Examples of C$_{1-5}$-alkyl groups are methyl, ethyl, propyl, isopropyl, n-butyl and isomers thereof and n-pentyl and isomers thereof. Cyclopropyl, cyclobutyl, cyclopentyl and cyclohexyl are examples of C$_{3-6}$-cycloalkyl groups. n-Pentyl, n-hexyl, n-heptyl, n-octyl, n-nonyl and n-decyl are examples of straight-chain C$_{5-10}$-alkyl groups. Isopropyl, sec.butyl, isobutyl and amyl are examples of branched C$_{3-5}$-alkyl groups. ω-Carboxypropyl is a preferred C$_{3-5}$-ω-carboxyalkyl group.

A preferred group of compounds of formula I comprises those in which R$^1$ is straight-chain C$_{5-10}$-alkyl, branched C$_{3-5}$-alkyl, C$_{3-6}$-cycloalkyl or C$_{3-5}$ω-carboxyalkyl.

Another preferred group of compounds of formula I comprises those in which R$^1$ is hydrogen, R$^2$ is C$_{3-5}$-ω-carboxyalkyl and R$^3$ is C$_{1-5}$-alkyl. As such, R$^2$ is preferably ω-carboxyalkyl and R$^3$ is preferably selected from C$_{1-3}$ alkyl with most preferably C$_1$ alkyl.

The compounds of formula I can be made in accordance with the invention by a) cyclizing a compound of the formula

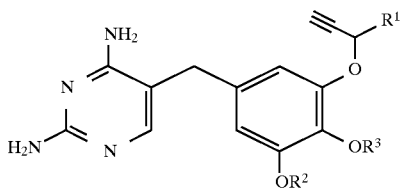

in which R$^1$, R$^2$ and R$^3$ have the above significance; or b) reacting a compound of the formula

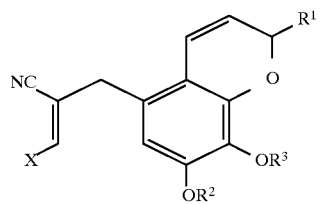

in which R$^1$, R$^2$ and R$^3$ have the above significance and X represents a leaving group, with guanidine and cleaving off protecting groups present, and, if desired, converting a thus-obtained compound of formula I into a pharmaceutically usable salt.

The cyclization in accordance with process variant a) can be carried out in a known manner known, e.g. by heating a compound of formula 11, conveniently in a high-boiling solvent such as N,N-diethylaniline, polyethylene glycol 400, nitrobenzene, o-dichlorobenzene or diphenyl ether, e.g. to about 180°–220° C.; or by treating it with a silver or mercury salt in a chlorinated solvent at about 20°–120° C. See in this respect W. K. Anderson and E. J. LaVoie, J. Org. Chem., 38, 3832 (1973), Chem. Reviews 84, 221–223 (1984) and S. M. Daluge, P. M. Skonezny, EP 0051879 (Nov. 11, 1981).

The reaction in accordance with process variant b) can also be effected in a known manner (see e.g. P. S. Manchand et al., J.Org. Chem. 57, 3531–3535 (1992)). Alkoxy such as methoxy, arylamino such as anilino and morpholino are examples of leaving groups X.

The compounds of formula I can also be in the form of pharmaceutically acceptable acid addition salts are made using organic and inorganic acids. Examples of acid addition salts of compounds of formula I are salts with mineral acids, for example hydrohalic acids such as hydrochloric acid, hydrogen bromide and hydrogen iodide, sulphuric acid, nitric acid, phosphoric acid and the like, salts with organic sulphonic acids, for example with alkyl- and arylsulphonic acids such as methanesulphonic acid, p-toluene-sulphonic acid, benzenesulphonic acid and the like, as well as salts with organic carboxylic acids, for example with acetic acid, tartaric acid, maleic acid, citric acid, benzoic acid, salicylic acid, ascorbic acid and the like.

The compounds of formula I which contain a carboxyl group also form pharmaceutically acceptable salts with bases. Examples of such salts of compounds of formula I are alkali metal salts, for example sodium and potassium salts, ammonium salts, salts with organic bases, for example with amines such as diisopropylamine, benzylamine, dibenzylamine, triethanolamine, triethylamine, N,N-dibenzylethylenediamine, N-methylmorpholine, pyridine, piperazine, N-ethylpiperidine, N-methyl-D-glucamine and procaine, or with amino acids such as arginine and lysine.

The compounds of formulae II and III are novel and are also objects of the invention. They can be prepared according to the following Reaction Schemes in which R$^1$, R$^2$, R$^3$ and X have the above significance.

Reaction Scheme 1

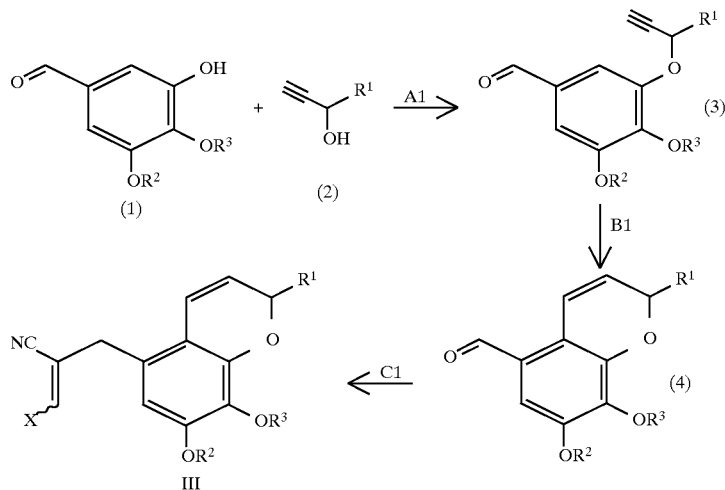

Reaction A1

This reaction can be carried out according to known methods (see e.g. O. Mitsunobu, Synthesis 1981, 1). It is preferably carried out in an inert solvent such as e.g. dichloromethane, tetrahydrofuran or toluene in a temperature range of −10° C. to +50° C. in the presence of triphenylphosphine and a dialkyl azodicarboxylate. Where the propargyl halide or tosylate corresponding to the alcohol (2) is accessible, a normal alkylation of the phenol group can also be carried out (see reaction D3).

Reaction B1

This reaction can also be carried out according to known methods in analogy to process variant a) described above for making of compounds of formula I.

Reaction C1

This reaction can also be carried out according to known methods. It is preferably carried out in an inert solvent such as e.g. dimethyl sulphoxide, N,N-dimethylformamide, etc. in a temperature range of 20° C. to 100° C. in the presence of a strong base such as potassium tert.-butylate or sodium hydride, see e.g. P. S. Manchand et al., J. Org. Chem. 57, 3531–3535 (1992).

Reaction A2

This reaction can also be carried out according to known methods (see D. R. M. Walton and F. Waugh, J. Organomet. Chem. 37, 45 (1972) and K. C. Nicolaou et al, J. Am. Chem. Soc., 106, 3548 (1984)). It is preferably carried out in an inert solvent such as e.g. dichloromethane in a temperature range of −30° C. to 0° C. in the presence of stoichiometric amounts of aluminum chloride and bis(trimethylsilyl)-acetylene.

Reaction B2

This reaction can also be carried out according to known methods (see A. L. Gemal and J.-L. Luche, J. Am. Chem. Soc., 103, 5454 (1981)).

Reaction C2

This reaction can also be carried out according to known methods.

Reaction D2

This reaction can also be carried out according to known methods. See J. A. Katzenellenbogen et al, J. Org. Chem. 54, 2624 (1991) (for $R^4$=tetramethylsilyl) and K. Mori et al., Liebigs Ann. 1991, 529.

Reaction Scheme 2

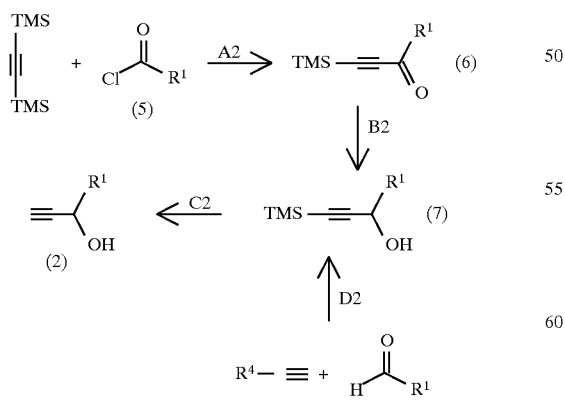

Reaction Scheme 3

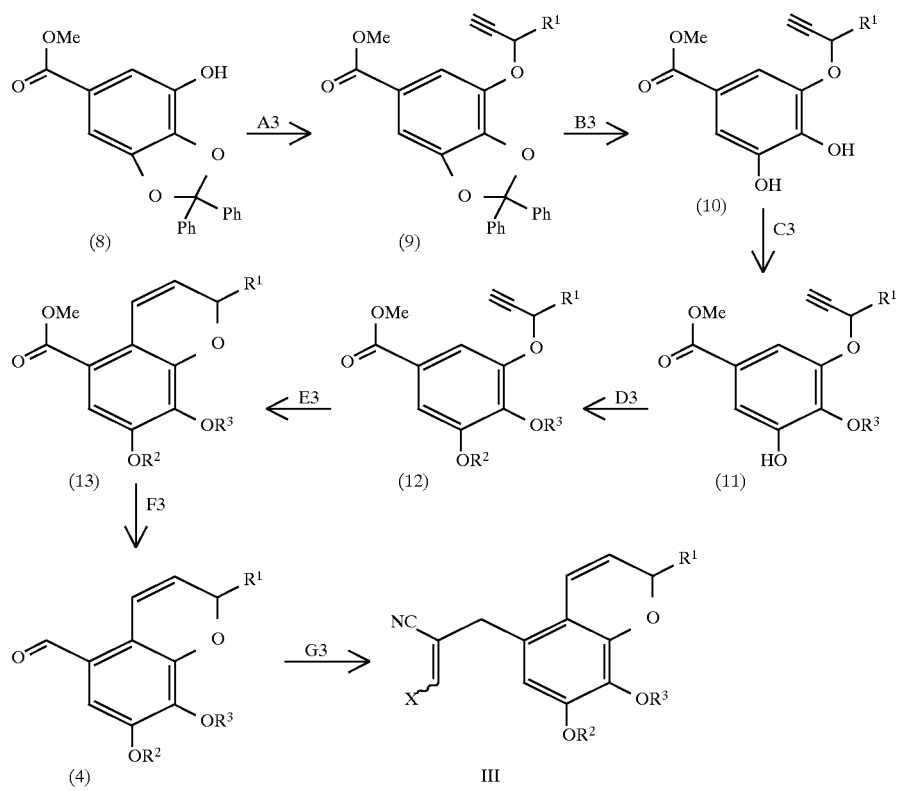

Reaction A3

This reaction is carried out analogously to reaction A1.

The starting material (8) is known, see L. Jurd, J. Am. Chem. Soc., 81, 4606 (1959).

Reaction B3

This reaction can also be carried out according to known methods. Preferably, compound (9) in an inert solvent such as e.g. dichloromethane, tetrahydrofuran or toluene is treated with a protic acid such as hydrochloric acid, sulphuric acid or trifluoroacetic acid in the presence of water in a temperature range of 20° C. to 100° C.

Reaction C3

A selective alkylation of the 4-hydroxy group in compound (11) can be accomplished by reaction with an alkyl iodide in the presence of a weak base such as sodium hydrogen carbonate at 0° C. to 30° C. in an aprotic dipolar solvent such as N,N-dimethylformamide.

Reaction D3

This reaction can also be carried out according to known methods. It can be carried out using an alkyl halide either in an inert solvent such as e.g. dimethyl sulphoxide, N,N-dimethyl-formamide, etc. in a temperature range of 10° C. to 50° C. in the presence of a strong base such as potassium tert.-butylate or sodium hydride, or in a polar solvent such as acetone, 2-butanone etc. in a temperature range of 50° C. to 100° C. in the presence of potassium carbonate.

Reaction E3

This reaction can also be carried out according to known methods analogously to variant a) of the process referred to a) above which involves cyclizing the compound.

Reaction F3

This reaction can be carried out in one step or in two steps according to known methods. The one-step method (see R. Kanazawa and T. Tokoroyama, Synthesis 1976, 526) is preferably carried out at −30° to −10° C. The two-step method involves a complete reduction to the corresponding alcohol with aluminum hydrides such as DIBALH or REDAL and subsequent re-oxidation to the aldehyde with activated manganese dioxide or by Swern oxidation with dimethyl sulphoxide/oxalyl chloride.

Reaction G3

This reaction corresponds to reaction C1.

Compounds of formula II can be prepared from compounds of the formula

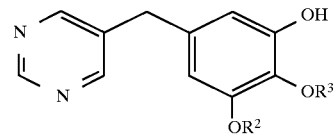

and compounds of formula (2) analogously to reaction A1.

Compounds of formula II can be prepared from compounds of formulae (2) and (14)

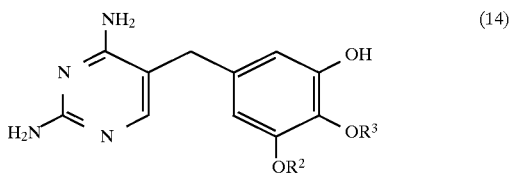

in analogy to reaction A1.

The preparation of compounds II and III is, moreover, described in the Examples.

As already mentioned, the compounds of formula I or their pharmaceutically acceptable salts have valuable antibacterial properties. They are active against a large number of pathogenic microorganisms such as e.g. *Staphylococcus aureus, Pneumocystis carinii* etc. by virtue of their activity in inhibiting bacterial dihydrofolate reductase (DHFR).

The inhibition of this enzyme was taken as a measurement for the antibacterial activity. It is determined using the method of Baccanari and Joyner (Biochemistry 20, 1710 (1981); see also P. G. Hartman et al., FEBS 242, 157–160 (1988).

The $IC_{50}$ values (concentration at which the enzyme is inhibited by 50%) are determined by means of a graph.

The following Table contains inhibitory concentrations obtained for representative members of the class of compound defined by formula I and determined in the above test. The $IC_{50}$ values ($\mu$M) against the purified DHFR of the reference strain *S. aureus* ATCC 25923 as well as against the purified DHFR of the multiresistant strain *S. aureus* 157/4696 are given. The third column shows the $IC_{50}$ values ($\mu$M) against the purified DHFR of the opportunistic pathogen *P. carinii*. The inhibition constants of trimethoprim (TMP) are also given as a comparison.

| Compound of Example No. | S. aureus ATCC 25923 | S. aureus 157/4696 | P. carinii |
|---|---|---|---|
| 6 | 0.005 | 0.770 | 0.220 |
| 7 | 0.016 | 0.850 | 2.800 |
| 8 | 0.001 | 1.000 | 1.000 |
| 9 | 0.001 | 0.900 | 3.000 |
| 10 | 0.005 | 0.520 | 0.040 |
| TMP | 0.007 | 2.250 | 5.500 |

The products in accordance with the invention can be used as medicaments, e.g. in the form of unit dosage pharmaceutical preparations for enteral or parenteral administration. For example, the products in accordance with the invention can be administered perorally, e.g. in the unit dosage forms of tablets, coated tablets, dragées, hard and soft gelatine capsules, solutions, emulsions or suspensions, rectally, e.g. in the form of suppositories, or parenterally, e.g. in the form of injection solutions.

The production of the pharmaceutical preparations can be effected in a manner which will be familiar to any person skilled in the art by bringing the substances in accordance with the invention, optionally in combination with other therapeutically valuable substances, into a galenical administration form together with suitable, non-toxic, inert, therapeutically compatible solid or liquid carrier materials and, if desired, the usual pharmaceutical adjuvants.

Both inorganic and organic carrier materials are suitable as such carrier materials. Thus, for example, lactose, corn starch or derivatives thereof, talc, stearic acid or its salts can be used as carrier materials for tablets, coated tablets, dragées and hard gelatine capsules. Suitable carriers for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and glucose. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols.

The usual preservatives, solubilizers, stabilizers, wetting agents, emulsifiers, sweeteners, colorants, flavorants, salts for varying the osmotic pressure, buffers, masking agents and anti-oxidants come into consideration as pharmaceutical adjuvants.

For parenteral administration the compounds of formula I and, respectively, their salts are preferably provided as lyophilizates or dry powders for dilution with usual carriers such as water or isotonic saline.

The compounds of formula I are distinguished by a high antibacterial activity and, respectively, a pronounced synergistic effect in combination with sulfonamides and good tolerance. They inhibit bacterial dihydrofolate reductase and potentiate the antibacterial activity of sulfonamides such as e.g. sulfisoxazole, sulfadimethoxine, sulfamethoxazole, 4-sulfanilamido-5,6-dimethoxy-pyrimidine (sulfadoxine), 2-sulfanilamido-4,5-dimethyl-pyrimidine, sulfaquinoxaline, sulfadiazine, sulfamonomethoxine, and 2-sulfanilamido-4,5-dimethyl-isoxazole and other inhibitors of enzymes which are involved in folic acid biosynthesis, such as e.g. pteridine derivatives. Such combinations of the compounds of formula I and either sulfonamides or inhibitors of enzymes involved in folic acid synthesis can be used in the control or prevention of illnesses such as infectious diseases.

Oral, rectal and parenteral administration come into consideration in human medicine for such combinations of one or more compounds I in accordance with the invention with sulfonamides. The ratio of compound I to sulfonamide can vary within a wide range and can be fitted to the individual requirements in each particular case. In general, the ratio can be from about 1:40 (parts by weight) to about 1:1 (parts by weight) with a preferred ratio of from about 1:10 to about 1:2.

Thus, e.g., a tablet can contain 80 mg of a compound I in accordance with the invention and 400 mg of sulfamethoxazole, a tablet for children can contain 20 mg of a compound I in accordance with the invention and 100 mg of sulfamethoxazole; syrup (per 5 ml) can contain 40 mg of compound I and 200 mg of sulfamethoxazole.

A daily dosage of about 0.2 g to about 2 g of a compound of formula I in accordance with the invention comes into consideration for adults.

The following Examples illustrate the invention in more detail. Examples 1–4 describe the preparation of starting materials of formulae II and III, while Examples 5–10 describe the preparation of the compounds of formula I. The temperatures are given in degrees Celsius.

EXAMPLE 1

Preparation of Compounds of Formula (2)

a) 29.3 g of aluminum(III) chloride were suspended in 300 ml of dichloromethane under argon and cooled to −30° C. A solution of 44.2 ml of bis(trimethylsilyl)acetylene and 18.3 ml of cyclopropanecarboxylic acid chloride were added at −30° C. over 15 min. The reaction mixture was left to warm to −10° C., poured into a vigorously stirred mixture of 250 ml of 3N HCl and 500 g of ice, stirred for a further 10 min. and finally extracted with 2×750 ml of hexane. The organic phases were washed in succession with in each case 750 ml of saturated NaCl, $NaHCO_3$ and NaCl. The organic phases were dried and evaporated. Distillation of the crude product at 95° C./14 mbar yielded 1-cyclopropyl-3-trimethylsilanyl-prop-2-yn-1-one as a colorless oil.

b) 37.3 g of Cer(III) chloride heptahydrate were added to a solution of 16.6 g of (RS)-1-cyclopropyl-3-trimethylsilanyl-prop-2-yn-1-one in 170 ml of methanol and the mixture was stirred at 20° C. until all had dissolved. Then, 1.9 g of sodium borohydride were added cautiously in portions in order to avoid excessive foaming.

The resulting white suspension was cooled to 10° C., treated with 50 ml of 1N HCl and then diluted with 150 ml of ice-water. This mixture was extracted with 2×400 ml of hexane. The hexane phases were washed with 300 ml of ice-water, dried (Na$_2$SO$_4$) and evaporated. Distillation of the crude product at 106° C./14 mbar gave (RS)-1-cyclopropyl-3-trimethylsilanyl-prop-2-yn-1-ol as a yellowish oil.

c) 7.8 g of (RS)-1-cyclopropyl-3-trimethylsilanyl-prop-2-yn-1-ol were dissolved in 80 ml of methanol, treated with 0.64 g of potassium carbonate and stirred at 20° C. for 3 hrs. Then, the methanol was removed on a rotary evaporator at 200 mbar/40° C. The residue was taken up in 80 ml of diethyl ether and extracted with 80 ml of ice-water. The crude product was distilled at 14 mbar/60° C. (with approximate precautions to avoid a possible danger of explosion). (RS)-1-Cyclopropyl-prop-2-yn-1-ol was obtained as a colorless oil.

d) In analogy to Example 1a), from glutaric acid monomethylester chloride there was obtained methyl 5-oxo-7-trimethylsilanyl-hept-6-ynoate.

e) In analogy to Example 1b), from methyl 5-oxo-7-trimethyl-silanyl-hept-6-ynoate there was obtained methyl (RS)-5-hydroxy-7-trimethylsilanyl-hept-6-ynoate.

f) In analogy to Example 1c), from methyl (RS)-5-hydroxy-7-trimethylsilanyl-hept-6-ynoate there was obtained methyl (RS)-5-hydroxy-hept-6-ynoate.

EXAMPLE 2

Preparation of Compounds of Formula (3)

a) 7.3 g of 3,4-dimethoxy-5-hydroxybenzaldehyde, 6.9 g of (RS)-1-cyclopropyl-3-trimethylsilanyl-prop-2-yn-1-ol and 10.5 g of triphenylphosphine were dissolved in 60 ml of toluene under argon and cooled to 5° C. A solution of 6.9 ml of diethyl azodicarboxylate in 20 ml of toluene was slowly added dropwise thereto at 5° C. over 50 min. The resulting reaction mixture was chromatographed directly on silica gel in toluene. There were obtained 4.2 g of a yellow oil (HPLC 80%). This was dissolved in 40 ml of methanol and stirred at 20° C. with 553 mg of potassium carbonate for 3 hrs. Extraction was effected with in each case 2×50 ml of ethyl acetate and water. For crystallization, it was dissolved in 10 ml of hot ethyl acetate and then diluted with 20 ml of hexane. There was obtained (RS)-3-(1-cyclopropyl-prop-2-ynyloxy)-4,5-dimethoxy-benzaldehyde as white crystals.

b) 63.6 g of methyl 3,4-dimethoxy-5-hydroxy-benzoate [E. Späth and H. Röder, Monatsh. für Chemie, 43, 93 (1923)], 38.5 g of (RS)-1-cyclopropyl-prop-2-yn-1-ol and 118 g of triphenylphosphine were dissolved in 600 ml of toluene under argon and cooled to 5° C. A solution of 70 ml of diethyl azodicarboxylate in 150 ml of toluene was slowly added dropwise thereto at 5° C. over 90 min. The mixture was stirred at 5° C. for a further 1 hr. and at 20° C. for 3 hrs. Then, 300 ml of toluene were distilled off on a rotary evaporator and the suspension obtained was stirred in an ice bath for 30 min. The separated triphenylphosphine oxide was filtered off and the filtrate was evaporated. The resulting oil was chromatographed on silica gel with hexane/ethyl acetate 4:1, then 3:1. Crystallization was effected from diethyl ether and hexane. There was obtained methyl (RS)-3-(1-cyclopropyl-prop-2-ynyloxy)-4,5-dimethoxy-benzoate as white crystals.

c) In analogy to Example 2a), from methyl (RS)-5-hydroxy-7-trimethylsilanyl-hept-6-ynoate there was obtained methyl (RS)-5-(5-formyl-2,3-dimethoxy-phenoxy)-hept-6-ynoate.

d) In analogy to Example 2a), from (RS)-1-octyn-3-ol there was obtained (RS)-3,4-dimethoxy-5-(1-pentyl-prop-2-ynyloxy)-benzaldehyde.

e) In analogy to Example 2a), from (RS)-4-methyl-1-pentyn-3-ol there was obtained (RS)-3-(1-isopropyl-prop-2-ynyloxy)-4,5-dimethoxy-benzaldehyde.

f) In analogy to Example 2a), from (RS)-5-methyl-1-hexyn-3-ol there was obtained (RS)-3-(1-isobutyl-prop-2-ynyloxy)-4,5-dimethoxy-benzaldehyde.

EXAMPLE 3

Preparation of Compounds of Formula (4)

a) 33.5 g of methyl (RS)-3-(1-cyclopropyl-prop-2-ynyloxy)-4,5-dimethoxy-benzoate were dissolved in 330 ml of N,N-diethylaniline, heated to 200° C. under argon and stirred at 200° C. for a further 5 hrs. The solvent was distilled off at 90° C./1 mbar and the residue was extracted: 2×1.5 l of diethyl ether, 2×1.5 l of 1N HCl, 2×1.5 l of saturated NaCl. The oil obtained was purified by silica gel chromatography with toluene, then toluene/ethyl acetate 9:1. Crystallization was effected from diethyl ether and hexane. Methyl (RS)-2-cyclopropyl-7,8-dimethoxy-2H-1-benzopyran-5-carboxylate was obtained as white crystals.

b1) 2.4 g of (RS)-3-(1-cyclopropyl-prop-2-ynyloxy)-4,5-dimethoxy-benzaldehyde were dissolved in 20 ml of N,N-diethyl-aniline, heated to 200° C. under argon and stirred at 200° C. for a further 1 hr. The solvent was distilled off at 90° C./1 mbar and the residue was extracted: 2×100 ml of diethyl ether, 2×100 ml of 1N HCl, 2×100 ml of saturated NaCl. The crude product was purified by two-fold silica gel chromatography with dichloromethane and, respectively, ethyl acetate/hexane 5:1. (RS)-2-Cyclopropyl-7,8-dimethoxy-2H-1-benzopyran-5-carbaldehyde was obtained as a brown oil (HPLC 96%).

b2) A solution of 48 ml of morpholine in 50 ml of toluene was added dropwise over 1 hr. under argon to an ice-cold solution of 143 ml of sodium dihydrido-bis-(2-methoxyethoxy) aluminate (3.5M in toluene) diluted with 200 ml of toluene. The resulting reduction solution was then added dropwise under argon during 1 hr. to a solution, cooled to −35° C., of 46 g of methyl (RS)-2-cyclopropyl-7,8-dimethoxy-2H-1-benzopyran-5-carboxylate in 200 ml of toluene and the mixture was stirred at −15° C. for a further 4 hrs. The reaction was stopped by the cautious addition of 40 ml of 3N NaOH and the mixture was left to warm. Extraction: 3×600 ml of ice-water, 1×600 ml of toluene. Chromatography: silica gel, hexane/ethyl acetate 5:1. Crystallization from diethyl ether/ hexane. (RS)-2-Cyclopropyl-7,8-dimethoxy-2H-1-benzopyran-5-carbaldehyde was obtained as a solid.

c) In analogy to Example 3a), from methyl (RS)-5-(5-formyl-2,3-dimethoxy-phenoxy)-hept-6-ynoate there was obtained methyl (RS)-4-(5-formyl-7,8-dimethoxy-2H-1-benzopyran-2-yl)-butyrate.

d) 1.5 g of methyl (RS)-4-(5-formyl-7,8-dimethoxy-2H-1-benzopyran-2-yl)-butyrate were dissolved in 10 ml of tetrahydrofuran under argon and then treated with 1 ml of 1N NaOH and stirred at 20° C. for 1.5 hrs. The reaction mixture was acidified with 9 ml of 1N HCl, saturated with NaCl and extracted with 2×20 ml of ethyl acetate. The crude product was chromatographed on silica gel in ethyl acetate and chromatographed from toluene/hexane 1:1 There was obtained (RS)-4-(5-formyl-7,8-dimethoxy-2H-1-benzopyran-2-yl)-butyric acid as white crystals.

e) In analogy to Example 3a), from (RS)-3,4-dimethoxy-5-(1-pentyl-prop-2-ynyloxy)-benzaldehyde there was obtained (RS)-7,8-dimethoxy-2-pentyl-2H-1-benzopyran-5-carbaldehyde.

f) In analogy to Example 3a), from (RS)-3-(1-isopropyl-prop-2-ynyloxy)-4,5-dimethoxy-benzaldehyde there was obtained (RS)-2-isopropyl-7,8-dimethoxy-2H-1-benzopyran-5-carbaldehyde.

g) In analogy to Example 3a), from (RS)-3-(1-isobutyl-prop-2-ynyloxy)-4,5-dimethoxy-benzaldehyde there was obtained (RS)-2-isobutyl-7,8-dimethoxy-2H-1-benzopyran-5-carbaldehyde.

EXAMPLE 4

Preparation of Compounds of Formula III 30g of (RS)-2-cyclopropyl-7,8-dimethoxy-2H-1-benzopyran-5-carbaldehyde and 17.5 g of 3-anilinopropionitrile were dissolved in 300 ml of dimethyl sulphoxide under argon, cooled to 10° C. and treated portionwise with 13.5 g of potassium tert.butylate. Subsequently, the mixture was stirred at 10° C. for a further 1 hr. and at 20° C. for 5 hrs. For the working up, the mixture was poured on to 3 l of ice/water and extracted: 2×3 l of ethyl acetate, 2×3 l of water. The crude product was purified by silica gel chromatography with hexane/ethyl acetate 5:1 to 2:1 and crystallized from hexane/ethyl acetate. (RS)-3-Anilino-2-(2-cyclopropyl-7,8-dimethoxy-2H-1-benzopyran-5-yl-methyl)acrylonitrile was obtained as white crystals, m.p. 140° C.

Example 5

1.45 g of guanidine hydrochloride were dissolved in 20 ml of ethanol, stirred with 1.7 g of potassium tert.butylate for 15 min. and then filtered through Dicalite. The filtrate was added to 2 g of (RS)-3-anilino-2-(2-cyclopropyl-7,8-dimethoxy-2H-1-benzopyran-5-yl-methyl)acrylonitrile and the mixture was boiled at reflux for 8 hrs. The product crystallized out spontaneously upon cooling. Recrystallization from 90 ml of ethanol gave (RS)-5-(2-cyclopropyl-7,8-dimethoxy-2H-1-benzopyran-5-yl-methyl)-pyrimidine-2,4-diamine as white crystals, m.p. 229° C.

EXAMPLE 6

In analogy to Examples 4 and 5, from (RS)-4-(5-formyl-7,8-dimethoxy-2H-1-benzopyran-2-yl)-butyric acid there was obtained (RS)-4-[5-(2,4-diamino-pyrimidin-5-ylmethyl)-7,8-dimethoxy-2H-1-benzopyran-2-yl]-butyric acid, m.p. 124° C.

EXAMPLE 7

In analogy to Examples 4 and 5, from (RS)-7,8-dimethoxy-2-pentyl-2H-1-benzopyran-5-carbaldehyde there was obtained (RS)-5-(7,8-dimethoxy-2-pentyl-2H-1-benzopyran-5-ylmethyl)-pyrimidine-2,4-diamine, m.p. 188° C.

EXAMPLE 8

In analogy to Examples 4 and 5, from 2-isopropyl-7,8-dimethoxy-2H-1-benzopyran-5-carbaldehyde there was obtained (RS)-5-(2-isopropyl-7,8-dimethoxy-2H-1-benzopyran-5-ylmethyl)-pyrimidine-2,4-diamine, m.p. 223° C.

EXAMPLE 9

In analogy to Examples 4 and 5, from (RS)-2-isobutyl-7,8-dimethoxy-2H-1-benzopyran-5-carbaldehyde there was obtained (RS)-5-(2-isobutyl-7,8-dimethoxy-2H-1-benzopyran-5-ylmethyl)-pyrimidine-2,4-diamine, m.p. 214° C.

EXAMPLE 10

In analogy to Examples 4 and 5, from tert-butyl 4-(5-formyl-8-methoxy-2H-1-benzopyran-7-yloxy)-butyrate via tert-butyl 4-[5-(2-cyano-3-phenylamino-allyl)-8-methoxy-2H-chromen-7-yloxy]-butyrate there was obtained 4-[5-(2,4-diamino-pyrimidin-5-ylmethyl)-8-methoxy-2H-1-benzopyran-7-yloxy]-butyric acid, m.p. 25° C.

EXAMPLE A

| Tablets | |
|---|---|
| Sulfamethoxazole | 400 mg |
| Compound of formula I, e.g. 4-[5-(2,4-diamino-pyrimidin-5-ylmethyl)-8-methoxy-2H-1-benzopyran-7-yloxy]-butyric acid | 80 mg |
| PRIMOJEL (starch derivative) | 6 mg |
| POVIDONE K30 (polyvinylpyrrolidone) | 8 mg |
| Magnesium stearate | 6 mg |
| Total weight | 500 mg |

EXAMPLE B

| | |
|---|---|
| Compound of formula I, e.g. 4-[5-(2,4-diamino-pyrimidin-5-ylmethyl)-8-methoxy-2H-1-benzopyran-7-yloxy]-butyric acid | 100 mg |
| Corn starch | 15 mg |
| Talc | 3 mg |
| Magnesium stearate | 2 mg |
| | 120 mg |

I claim:
1. A compound of formula I

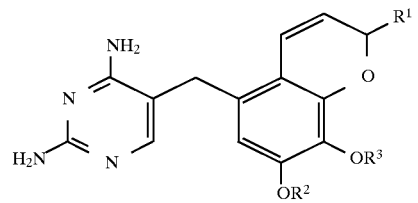

wherein either $R^1$ is straight-chain $C_{5-10}$-alkyl, branched $C_{3-5}$-alkyl, $C_{3-6}$-cycloalkyl or $C_{3-5}$-ω-carboxyalkyl and each of $R^2$ and $R^3$ is $C_{1-5}$alkyl; or $R^1$ is hydrogen, $R^2$ is $C_{3-5}$-ω-carboxyalkyl and $R^3$ is $C_{1-5}$-alkyl;

or their pharmaceutically acceptable acid addition salts.

2. The compound of claim 1, in which $R^1$ is straight-chain $C_{5-10}$-alkyl, branched $C_{3-5}$-alkyl, $C_{3-6}$-cycloalkyl or $C_{3-5}$-ω-carboxyalkyl, and each of $R^2$ and $R^3$ is $C_{1-5}$-alkyl.

3. The compound of claim 1 in which $R^1$ is hydrogen, $R^2$ is $C_{3-5}$-ω-carboxyalkyl, and $R^3$ is $C_{1-5}$ alkyl.

4. The compound of claim 2, (RS)-5-(2-cyclopropyl-7,8-dimethoxy-2H-1-benzopyran-5-ylmethyl)-pyrimidine-2,4-diamine.

5. The compound of claim 2, (RS)-4-[5-(2,4-diamino-pyrimidin-5-ylmethyl)-7,8-dimethoxy-2H-1-benzopyran-2-yl]-butyric acid.

6. The compound of claim 2, (RS)-5-(7,8-dimethoxy-2-pentyl-2H-1-benzopyran-5-ylmethyl)-pyrimidine-2,4-diamine.

7. The compound of claim 2, (RS)-5-(2-isopropyl-7,8-dimethoxy-2H-1-benzopyran-5-ylmethyl)-pyrimidine-2,4-diamine.

8. The compound of claim 3, (RS)-5-(2-isobutyl-7,8-dimethoxy-2H-1-benzopyran-5-ylmethyl)-pyrimidine-2,4-diamine.

9. The compound of claim 3, 4-[5-(2,4-diaminopyrimidin-5-ylmethyl)-8-methoxy-2H-1-benzopyran-7-yloxy]-butyric acid.

10. A pharmaceutical composition comprising a therapeutically effective amount of a compound of formula I

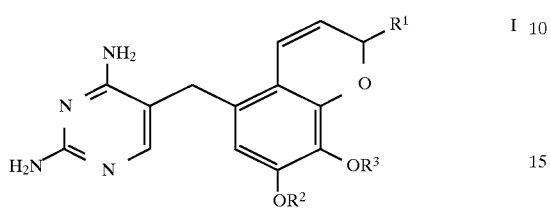

wherein either $R^1$ is straight-chain $C_{5-10}$-alkyl, branched $C_{3-5}$-alkyl, $C_{3-6}$-cycloalkyl or $C_{3-5}$-ω-carboxyalkyl and each of $R^2$ and $R^3$ is $C_{1-5}$-alkyl; or $R_1$ is hydrogen, $R^2$ is $C_{3-5}$-ω-carboxyalkyl and $R^3$ is $C_{1-5}$-alkyl;

or their pharmaceutically acceptable acid addition salts, and a pharmaceutically acceptable carrier.

11. The composition of claim 10 wherein $R^1$ is straight-chain $C_{5-10}$-alkyl, branched $C_{3-5}$-alkyl, $C_{3-6}$cycloalkyl or $C_{3-5}$-ω-carboxyalkyl, and each of $R^2$ and $R^3$ is $C_{1-5}$-alkyl.

12. The composition of claim 10, wherein $R^1$ is hydrogen, $R^2$ is $C_{3-5}$-ω-carboxyalkyl and $R^3$ is $C_{1-5}$-alkyl.

13. A method of treating bacterial infections in a mammal in need of such treatment which comprises administering a therapeutically effective amount of a compound of formula 1

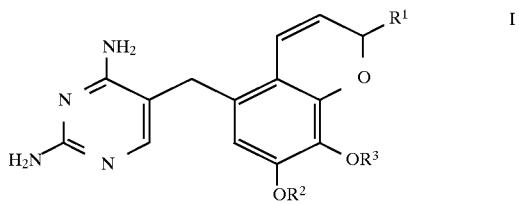

wherein either $R^1$ is straight-chain $C_{5-10}$-alkyl, branched $C_{3-5}$-alkyl, $C_{3-6}$cycloalkyl or $C_{3-5}$-ω-carboxyalkyl and each of $R^2$ and $R^3$ is $C_{1-5}$-alkyl; or $R^1$ is hydrogen, $R^2$ is $C_{3-5}$-ω-carboxyalkyl and $R^3$ is $C_{1-5}$-alkyl;

or their pharmaceutically acceptable acid addition salts, and a pharmaceutically acceptable carrier.

* * * * *